US006207038B1

(12) United States Patent
Steil et al.

(10) Patent No.: US 6,207,038 B1
(45) Date of Patent: Mar. 27, 2001

(54) PROCESS FOR PREPARING A COMPOSITE ELECTROLYTE BASED ON BIMEVOX AND THE USE OF SAID COMPOUND IN SEPARATING OXYGEN FROM A GAS MIXTURE

(75) Inventors: César Marlu Steil, Grenoble Cedex; Jacques Fouletier; Michel Kleitz, both of Grenoble; Gilles Lagrange, Forges les Bains; Pascal Del Gallo, Gif sur Yvette; Gaëtan Mairesse; Jean-Claude Boivin, both of Villeneuve D'Ascq, all of (FR)

(73) Assignee: L'Air Liquide, Societe Anonyme pour l'Etude et l'Exploitaion des Procedes Georges Claude, Paris (FR)

( * ) Notice: Subject to any disclaimer, the term of this patent is extended or adjusted under 35 U.S.C. 154(b) by 0 days.

(21) Appl. No.: 09/346,308

(22) Filed: Jul. 2, 1999

(30) Foreign Application Priority Data

Jul. 3, 1998 (FR) .................................................. 98 08522

(51) Int. Cl.[7] ...................................................... C25C 1/10
(52) U.S. Cl. ........................ 205/634; 205/636; 204/291; 204/421; 204/252; 252/519.13; 252/520.4; 429/33; 429/231.5; 429/304; 429/305; 264/125; 95/45; 95/54; 55/523
(58) Field of Search .................................... 205/634, 636; 204/291, 421, 252; 252/519.3, 520.4; 429/33, 304, 305, 231.5; 264/125; 55/523; 95/45, 54

(56) References Cited

U.S. PATENT DOCUMENTS

| 4,675,260 | * | 6/1987 | Sakurai et al. | ...................... 429/304 |
| 5,227,257 | * | 7/1993 | Abraham et al. | ...................... 429/33 |
| 5,273,628 | * | 12/1993 | Liu et al. | ...................... 429/33 |
| 5,785,839 | | 7/1998 | Kleitz et al. | ...................... 205/634 |

FOREIGN PATENT DOCUMENTS

WO95/32050  3/1995 (WO).

OTHER PUBLICATIONS

Search Report issued in French Application No. FR 98 08522.

\* cited by examiner

*Primary Examiner*—Bruce F. Bell
(74) *Attorney, Agent, or Firm*—Burns, Doane, Swecker & Mathis, L.L.P.

(57) ABSTRACT

A process for preparing a solid composite electrolyte comprising at least one compound of the BIMEVOX family is provided. The process comprises at least one step of preparing a mixture of one or more compounds of the BIMEVOX family with one or more chemically inert compounds, at least one step of compacting the mixture obtained, and at least one sintering step during which the temperature reached, over a nonzero time interval, has a value greater than the optimum sintering temperature for the compound of the BIMEVOX family.

19 Claims, 3 Drawing Sheets

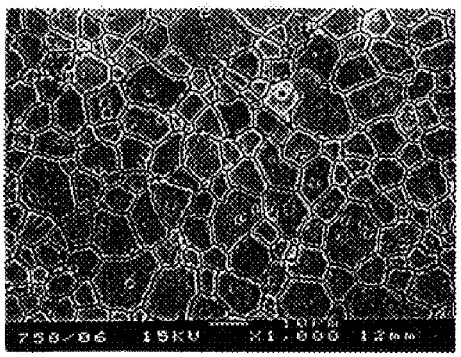
FIG. 3A  10 μm
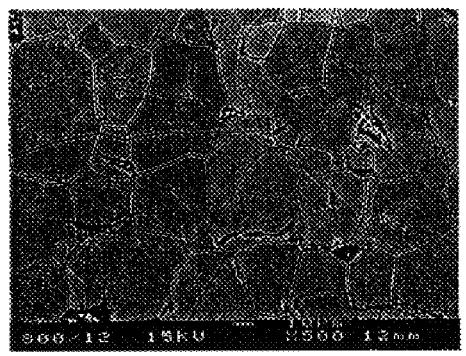
FIG. 3B  10 μm
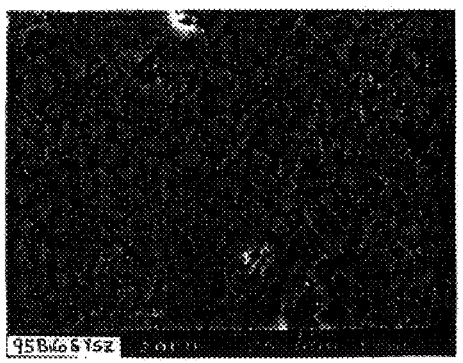
FIG. 3C  1 μm
FIG. 3D  1 μm

PROCESS FOR PREPARING A COMPOSITE ELECTROLYTE BASED ON BIMEVOX AND THE USE OF SAID COMPOUND IN SEPARATING OXYGEN FROM A GAS MIXTURE

BACKGROUND OF THE INVENTION (i) Field of the Invention

The subject of the invention is a process for preparing a solid composite electrolyte consisting of at least one compound of the BIMEVOX family and the use of said composite for extracting oxygen from air or from a gas mixture containing oxygen.

(ii) Description of Related Art

In order to separate oxygen from air or from a gas mixture containing it, by means of a solid-electrolyte cell or membrane, whether using a purely electrochemical process generated by a current generator or using an electrochemical semipermeability process generated by the difference in oxygen partial pressure between each of the faces of the cell or membrane, the solid electrolytes used are generally stabilized zirconias, such as those described for example in United States Patent published under the number U.S. Pat. No. 4,879,016, or oxides derived from $Bi_4V_2O_{11}$, such as those described in the International Patent Application published under the number WO 91/01274 and known by the generic name BIMEVOX. The latter, in which a variable fraction of the vanadium is replaced with a metal chosen especially from alkaline-earth metals, transition metals, rare earths or elements of Groups III to V of the Periodic Table of the Elements, are $O^{2-}$ ionic conductors and their anionic conductivity at 500° C. is of the same order of magnitude as that of stabilized zirconias at 800° C. The partial substitution of the constituent elements of $Bi_4V_2O_{11}$ stabilizes the gamma-phase structural type and maintains, in the $O^{2-}$ ion lattice, a vacancy content sufficient to allow anionic conductivity. Since the oxygen atoms of the $Bi_{2-x}M_yO_2$ layers strongly bonded to the bismuth atoms cannot move, it therefore means that the conductivity is essentially two-dimensional; the anionic conductivity of this phase is remarkable since it reaches $10^{-3}$ $\Omega^{-1}cm^{-1}$ at about 200° C.

These BIMEVOX compounds are used in electrochemical cells, like those described in the International Patent Applications published under numbers WO 94/06544 and WO 94/06545, and in cells operating by electrochemical semipermeability, such as those described in French Patent Application published under the number FR 2,698,016.

However, obtaining the intrinsic properties of these BIMEVOX-based electrolytes, whether mechanical or electrical properties, is conditional on proper control of the parameters for their synthesis. The term "synthesis parameters" should be understood to mean essentially the size of the initial particles and, during sintering the temperatures, rates of temperature rise and fall and the durations of any temperature hold at a given temperature. Likewise, depending on the metal chosen as the dopant and on its content, between 0% and 50%, it is necessary for the sintering conditions to be defined very precisely. These conditions have a direct influence on the particle size of the sintered material, this size itself governing the stability and the quality of the electrical and mechanical properties of the BIMEVOX compound. It has also been found that increasing the sintering temperatures by a few tens of degrees, for example 800° C. instead of 750° C. in the case of $Bi_2Co_{0.1}V_{0.9}O_{3.55}$, called hereafter BICOVOX. 10, has the effect of modifying the electrical properties of the material and that too great a temperature in this has the effect of favoring abnormal crystalline grain growth in BIMEVOX, therefore leading to a microstructure in the inhomogeneous material in which the average grain size exceeds the critical value of 5 $\mu$m. Under these conditions, on the one hand the mechanical properties degrade and the electrical resistivity increases, and on the other hand the electrical properties are no longer either stable over time or during thermal cycles.

In addition, poor adhesion of the electrode to the electrolyte in an elementary electrochemical cell of the BIMEVOX electrolyte/volume electrode type, such as the one described in the International Patent Application published under the number WO 95/32050, may be observed, and debonding phenomena have been demonstrated during operation of the cell. Thus, it has been possible to show that the adhesion of a composite electrode of the $LSM-Bi_2Co_{0.1}V_{0.9}O_{5.35}$ type (30% by volume) to an electrolyte of composition $Bi_2Co_{0.1}O_{5.35}$ after heating at 750° C., which is the maximum temperature for preventing abnormal grain growth of the electrolyte, is very poor.

The Applicant has therefore sought to develop a process for preparing a solid electrolyte comprising at least one compound of the BIMEVOX family which allows grain size of the material after sintering to be controlled and which thus results in mechanical properties that are superior compared to said BIMEVOX material alone, without the electronic and ionic properties of said material thereby suffering.

SUMMARY AND OBJECTS OF THE INVENTION

The problems explained above are solved by the implementation of the process which forms the subject of the present invention.

The subject of the invention is a process for preparing a solid composite electrolyte consisting of at least one compound of the BIMEVOX family, which process comprises:

a) at least one step of preparing a mixture of one or more compounds of the BIMEVOX family with one or more chemically inert compounds;

b) at least one step of compacting the mixture obtained from step a); and c) at least one sintering step during which the temperature reaches, over a nonzero time interval, a value greater than the optimum sintering temperature for said compound of the BIMEVOX family.

BRIEF DESCRIPTION OF THE DRAWINGS

FIG. 3 is a series of SEM micrographs which show the microstructure of specimens (a), (b), (c) and (d) of the examples.

DETAILED DESCRIPTION OF PREFERRED EMBODIMENTS OF THE INVENTION

Figure 1:
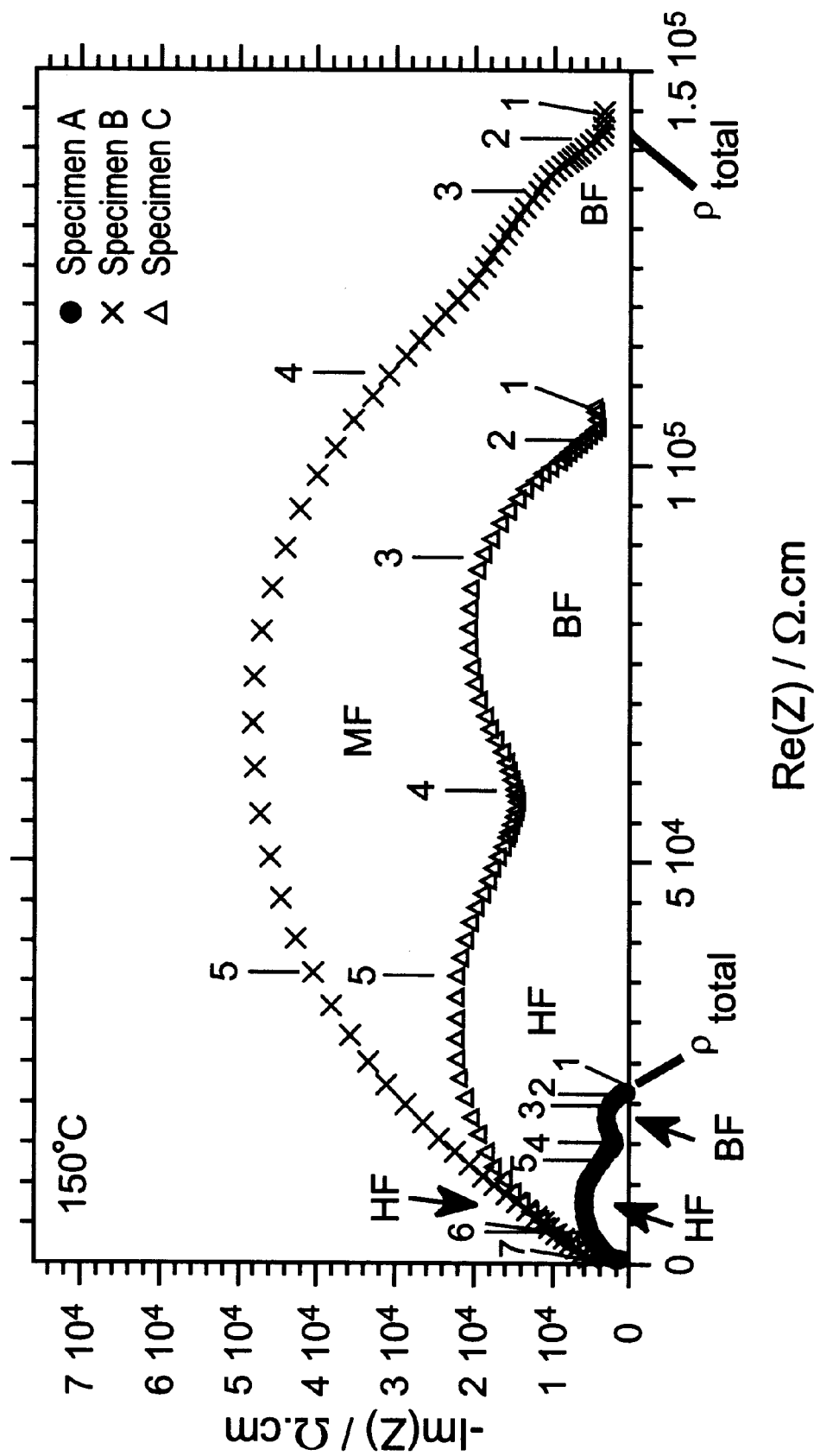
FIG. 1 is an impedance plot for BIMEVOX-based cell specimens (a), (b) and (c) of the examples.

The process for preparing a solid composite electrolyte comprising at least one compound of the BIMEVOX family includes a) at least one step of preparing a mixture of one or more compounds of the BIMEVOX family with one or more chemically inert compounds, b) at least one step of compacting the mixture obtained from step a), and c) at least one sintering step during which the temperature reached, over a nonzero time interval, has a value greater than the optimum sintering temperature for the compound of the BIMEVOX family.

The expression "at least one compound of the BIMEVOX family" should be understood to mean that it may be only one of the said compounds or a mixture thereof. The generic term "BIMEVOX" is used to denote oxides derived from $Bi_4V_2O_{11}$ in which a variable fraction of the vanadium is replaced with a metal, and especially compounds of formula (I):

$$(Bi_{2-x}M_xO_2)(V_{1-y}M'_yO_x) \qquad (I)$$

in which:

M represents one or more metals substituting for bismuth, chosen from those having an oxidation number of less than or equal to 3; and M' represents one or more elements substituting for vanadium, chosen from those having an oxidation number of less than, equal to or greater than 5, the limiting values of x, y, and therefore z, depending on the nature of the substituent elements M and M'.

Among the compounds of formula (I) as defined above, mention may be made of those in which only the vanadium atom is partially substituted with one or more elements. These compounds therefore satisfy the formula (II):

$$(Bi_2O_2)(V_{1-y}M'_yO_z) \qquad (II)$$

in which M' is as defined above, y being nonzero and more particularly greater than or equal to approximately 0.5 and less than or equal to 0.5.

M' is advantageously selected from alkali metals, alkaline-earth metals, transition metals, elements of Groups III to V of the Periodic Table of the Elements, or from the rare earths. When M' represents a transition metal, it is more particularly chosen from zinc, copper, manganese, nickel, cobalt, iron and cadmium atoms. When M' represents an alkaline-earth metal, it is more particularly chosen from calcium, strontium and barium atoms. As metal having a degree of oxidation equal to 3, M' may also represent an indium, aluminum or antimony atom. As metal having a degree of oxidation equal to 4, M' may also represent a tin, titanium or ruthenium atom. As metal having a degree of oxidation equal to 5, M' may also represent a niobium, tantalum or phosphorus atom. M' may also represent an alkali metal such as sodium or, as metal having a degree of oxidation equal to 2, it may represent a Pb atom. Among compounds of formula (I) as defined above, mention may be made of those in which the bismuth atom alone is partially substituted with one or more metals. These derivatives then satisfy the formula (III):

$$(Bi_{2-x}M_xO_2)(VO_z) \qquad (III)$$

in which x is nonzero and M is as defined above and more particularly chosen from rare earths, such as lanthanum.

Mention may also be made among compounds of formula (I) of those in which the oxygen atom is partially substituted with fluorine, or else those having mixed substitutions for the bismuth and for vanadium and corresponding to the formula (I) above in which x and y are nonzero, and more particularly compounds of formula (IV):

$$(Bi_{2-x}Pb_xO_2)(V_{1-y}Mo_yO_z) \qquad (IV)$$

The expression "chemically inert compounds" should be understood to mean any compounds not interacting chemically with the BIMEVOX compound or compounds. The materials chosen are more particularly carbides such as tungsten carbide or silicon carbide, nitrides such as silicon nitride, or oxides such as titanium oxide, alumina or $BiVO_4$ or zirconia, cerium oxide, hafnium oxide or thoria, said zirconia, cerium oxide, hafnium oxide or thoria being stabilized by one or more compounds chosen from yttrium oxide, barium oxide, magnesium oxide, calcium oxide, strontium oxide, scandium oxide and lanthanum oxide. The example given below illustrates the use, as inert compound, of zirconia stabilized with yttrium oxide, called yttria-stabilizied zirconia YSZ.

Step a) of the process described above consists either in mechanically mixing the BIMEVOX compound or compounds with one or more chemically inert compounds or in depositing, by successive impregnation, one or more precursor salts containing the chemically inert agent or agents and then in calcining in air. In the latter case, the oxide particles, for example zirconium or titanium oxide particles, after calcining, are relatively uniformly dispersed on the surface of the BIMEVOX compound or mixture of BIMEVOX compounds. According to a variant of step a), the chemically inert compound or compounds are added during the synthesis of the BIMEVOX compound or compounds, either in the form of an oxide if this synthesis is carried out by a solid-solid route, or in the form of a salt if this synthesis is carried out by coprecipitation.

In a general but nonlimiting manner, the mixture from step a) of the process as defined above comprises up to 30% by volume of the chemically inert compound and step a) is implemented using starting compounds having an average grain size of approximately 1 μm ($10^{-6}$ meter).

In a general but nonlimiting manner, step b) of the process as defined above is carried out at a compacting pressure of between 1500 bar and 4000 bar; the mixture thus compacted has a degree of compactness in the green state of between approximately 30% and 70%. The expression "optimum sintering temperature" should be understood to mean, in step c) of the process as defined above, the temperature that can be reached by a given material—in the present case a BIMEVOX compound or a mixture of BIMEVOX compounds—by controlling the crystalline growth until the grain size after sintering is less than 5 μm and preferably less than 3 μm. Step c) of the process as defined above is especially carried out at a temperature that may generally exceed 700° C., often 800° C., and more particularly greater than 820° C.

According to another aspect of the present invention, the subject of the latter is an electrochemical cell in which the solid electrolyte, consisting of one or more BIMEVOX derivatives mixed with one or more chemically inert compounds called hereafter "immiscible phase" or "inert phase", is obtained by the process as defined above and is either in contact with two so-called volume electrodes, respectively an anode and a cathode, which are porous to the gases, or itself has a homogeneous structure consisting of one or more composite solid electrolyte derivatives (BIMEVOX+ immiscible phase) with dynamic electrodes created in situ which are reversible and self-adaptive.

The expression "homogeneous structure" should be understood to mean in the above definition that, unlike in the devices of the prior art, such as the volume-electrode cell mentioned above, which consist of a solid electrolyte and two electrodes connected to current collectors, it being possible for said electrodes to be physically distinguished from said electrolyte, the homogeneous structure is a core of one or more BIMEVOX compounds behaving both as an electrolyte and as electrodes. In the above definition, those skilled in the art will easily appreciate the difference between a current collector, the function of which is solely to allow the electric current to flow by providing electrons at the cathode and by collecting them at the anode, and an electrode, the function of which is to catalyze the electrochemical dissociation.

The expression "dynamic electrodes created in situ" should be understood to mean in the above definition that the electronic conductivity is due to the transformation:

vanadium(V)→vanadium(IV)

on the cathode side.

The expression "created in situ" should be understood to mean in the above definition that the homogeneous structure becomes an electrode/electrolyte/electrode structure only by applying a nonzero potential difference to the opposed faces of said device; in the explanation below, reference will be made to "electrode zones" and "electrolyte zone" of said structure.

The term "reversible" should be understood to mean in the present definition that the device can operate in one direction or the other by simply reversing the polarity of the current generator.

The expression "self-adaptive" should be understood to mean that the device adapts by itself to the two types of functions mentioned above, namely the dynamic function and the reversibility function.

Those skilled in the art will also appreciate that one of the advantages of the homogeneous structure employed in the process, forming the subject of the present invention, is that the thickness of the "electrode zones" and of the "electrolyte zone" of said structure varies, especially depending on the temperature and on the intensity of the electric current which are applied to it, and that this dynamic nature thus makes it possible to regulate the rate of oxygen extraction.

According to another aspect of the present invention, the subject of the latter is a ceramic membrane operating according to the electrochemical semipermeability principle, in which this ceramic membrane, which conducts via $O^{2-}$ ions and consists of one or more BIMEVOX derivatives mixed with one or more chemically inert compounds, called hereafter immiscible phase, is obtained by the process as defined above.

When the cell as defined above, based on solid electrolytes, operates by electrochemistry, it is inserted into a circuit for supplying electric current, allowing the creation of a potential difference between its opposed faces by means of current collectors. These current collectors, which both deliver electrons at the cathode and remove them at the anode, must of course be made of a metal or of a metal alloy compatible with the BIMEVOX compounds, such as, for example, gold, silver, platinum, palladium, copper or stainless steel. The shape of the current collectors is determined so as to optimize the delivery of electrons at the cathode and their removal at the anode. It is generally a grid, a lacquer or a tip; if necessary, a nonzero portion of each of the current collectors of the electrochemical cell used lies inside the electrode layer or, as the case may be, the homogeneous structure; when the collector is a grid, it preferably has several tens of nodes per $cm^2$.

The electrochemical cell used is especially a plane structure with parallel faces or a hollow cylindrical structure of circular or oval cross section, having two coaxial cylindrical faces. An elementary electrochemical cell with volume electrodes may be represented by the scheme (A):

CC/BIMEVOX'–EC'/composite electrolyte(BIMEVOX+inert phase)/BIMEVOX"–EC"/CC'     (A)

in which CC and CC' represent the anode and cathode current collectors, BIMEVOX'–EC' and BIMEVOX"–EC" represent the two constituents characteristic of the volume electrodes in varying proportions, i.e. on the one hand a BIMEVOX compound and/or on the other hand an electronic conductor (EC), especially a metal or a metal oxide. This metal or the metal of the metal oxide may differ from or be the same as the metals of the BIMEVOX compounds. Likewise, the metals ME' and ME" of the BIMEVOX' and BIMEVOX" may be the same as or different from that or those contained in the BIMEVOX-inert phase composite electrolyte. The proportions by weight vary, for example, from 0 to 100% of one of the constituents of the volume electrode and from 100% to 0% of the other (if other chemical compounds also possibly present in the volume electrodes are ignored). An elementary electrochemical cell with reversible self-adaptive dynamic electrodes created in situ may be represented by the scheme (B):

CC/(BIMEVOX'+inert phase)/(ELECTROLYTE+inert phase)/BIMEVOX"+inert phase/CC     (B)

in which "ELECTROLYTE" represents the solid and gas-impermeable BIMEVOX "electrolyte zone", CC represents the current collectors and BIMEVOX' and BIMEVOX" represent the two constituents characteristic of the "electrode zones". The metals ME' and ME" and the BIMEVOX' and BIMEVOX" compounds may be the same as or different from that or those contained in the BIMEVOX/inert phase composite electrolyte.

The subject of the invention is also a composition consisting of a mixture containing at least 70% by volume of one or more compounds of the BIMEVOX family with up to 30% by volume of at least one or more chemically inert compounds chosen from carbides such as tungsten carbide or silicon carbide, nitrides such as silicon nitride, or oxides such as titanium oxide, alumina, $BiVO_4$, zirconia, cerium oxide, hafnium oxide, thoria, said zirconia, cerium oxide, hafnium oxide or thoria being stabilized by one or more compounds chosen from yttrium oxide, barium oxide, magnesium oxide, calcium oxide, strontium oxide, scandium oxide and lanthanum oxide, particularly a composition as defined above in which the compound of the BIMEVOX family is a compound of formula (II):

$$(Bi_2O_2)(V_{1-y}M'_yO_z) \quad\quad\quad (II)$$

in which M' represents a transition metal chosen from zinc, copper, manganese, nickel, cobalt, iron and cadmium atoms and y is greater than or equal to approximately 0.05 and less than or equal to approximately 0.5, and most particularly a composition containing from 90 to 95% by volume of $Bi_2Co_{0.1}V_{0.9}O_{5.35}$ and from 5 to 10% by volume of yttrium-stabilized zirconia YSZ.

In general, the devices, using a solid electrolyte prepared by the process as defined above, are used for extracting oxygen from a gas mixture or for analyzing the oxygen present in a given gas atmosphere.

It is also possible either to produce ultrapure oxygen or, for applications requiring oxygen-free atmospheres such as the electronic components industry or the food industry, to remove the oxygen from said atmosphere, said gaseous atmosphere lying above a liquid or a solid.

By way of nonlimiting example, the process is used to remove oxygen from the gaseous atmosphere lying above food products, especially fresh food products, or above oil baths for frying, in order to improve their preservation.

The experimental part described below illustrates the invention, without however limiting it.

EXPERIMENTAL PART

A—Preparation of the Specimens

In order to demonstrate the importance of the second phase on the crystalline grain growth and therefore on the mechanical and electrical properties of the materials, four BIMEVOX-based cells, with a ME content of 10%, were produced. The BIMEVOX compound chosen is $Bi_2Co_{0.1}V_{0.9}O_{5.35}$ (called BICOVOX.10). After the powder has been synthesized, the average particle size is less than or equal to one micron. Four materials were tested:

Specimen (a): $Bi_2Co_{0.1}V_{0.9}O_{5.35}$ (sintering: 750° C./0.5 h)

Specimen (b): $Bi_2Co_{0.1}V_{0.9}O_{5.35}$ (sintering: 820° C./12 h)

Specimen (c): $Bi_2Co_{0.1}V_{0.9}O_{5.35}/(5\%)$ YSZ (mechanical mixing+sintering: 830° C./4 h)

Specimen (d): $Bi_2Co_{0.1}V_{0.9}O_{5.35}/(10\%)$ YSZ (mechanical mixing+sintering: 850° C./4 h).

The operating conditions for preparing each of these specimens, whether they be they be the rates of temperature rise and fall, the uniaxial precompaction or the isostatic pressing, are identical; only the final sintering temperatures are different depending on the specimen prepared.

The final compactnesses obtained vary between 95 and 97%. The pills, after forming and sintering, are covered by gold electrodes deposited in the form of a lacquer. Once the latter has been applied, it is dried at about 100° C. The organic binder is removed by firing at 700° C./0.5 h.

B—Analysis of the Specimens

1) Analysis of SEM micrographs (FIG. 3).

The microstructure of the sintered materials was characterized by scanning electron microscopy (SEM). The electrical properties of the materials were determined firstly by impedance spectroscopy at 150° C. and then by conductivity measurements carried out between 150 and 600° C. Analysis of the SEM micrographs of the first three specimens shows:

for specimen (a), a homogeneous microstructure, the maximum grain size of which does not exceed 10 μm;

for specimen (b), an inhomogeneous microstructure with the presence of grains of a few tens of microns in size and having cracks. The presence of these cracks is due to a high abnormal crystalline growth of the material during sintering at temperatures above 750° C.;

for specimen (c) and (d), quite homogeneous microstructures, similar to that of specimen (a); the grain sizes are less than 5 μm. The addition of the second phase (in this case, stabilized zirconia) has proved to be effective in blocking the BIMEVOX grains at high temperature (>820° C.) and increases the mechanical strength (no cracks).

2) Electrical characterization.

FIG. 1 gives the impedance plots for specimens (a), (b) and (c) at 150° C.:

for specimen (a), two well-defined and well-separated circular arcs are observed. The first circular arc, observed at high frequencies (HF), is assigned to the intragranular properties of the material. The second circular arc, appearing at low frequencies (LF), corresponds to immobilization of the charge carriers due to the grain boundaries;

for specimen (b), the presence of a third semicircle at intermediate frequencies (MF) is observed. Because the average grain size is significantly greater than the 10 μm critical size, the total resistivity of the specimen is 7 times higher that that of specimen (a). In addition, the total resistivity varies over time and during thermal cycles;

for specimen (c), the plot has the same appearance as that for specimen (a). From this it may be deduced that the presence of the second phase, by preventing crystalline growth of the BICOVOX.10 grains at 830° C., makes it possible to stabilize the electrical properties of the material, while allowing the latter to be sintered at temperatures greater than 800° C. The total resistivity increases only by a factor of 5 compared with that of specimen (a).

3) Variation in conductivity with temperature.

Figure 2:
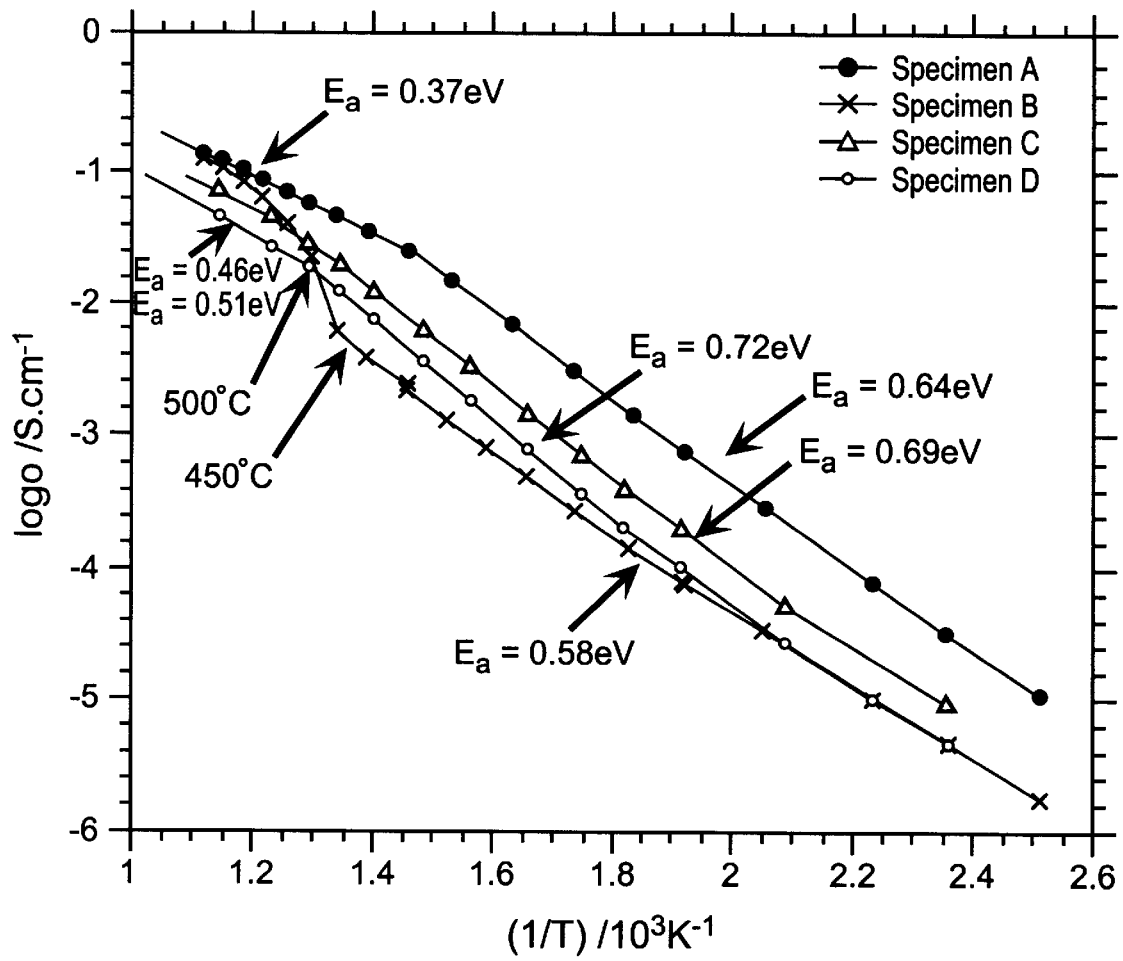
FIG. 2 is an Arrhenius plot illustrating the variation in conductivity with temperature for BIMEVOX-based cell specimens (a), (b), (c) and (d) of the examples.

FIG. 2 makes it possible to compare the electrical conductivities of specimens (a), (b), (c) and (d) as a function of temperature, plotted as an Arrhenius plot.

Specimen (b) exhibits the curve generally observed in the case of such materials, with a conductivity "jump" at about 450° C.

Specimen (a) exhibits an Arrhenius curve without a conductivity jump at about 450° C., with only a change in activation energy (from 0.37 eV at high temperature to 0.64 eV at a temperature below 400° C.). The curve is completely reversible during thermal cycles. In addition, the conductivity at ordinary temperature is seven times higher than in the case of specimen (b).

In the case of specimens (c) and (d), the curves do not show, unlike that for specimen (b), a conductivity jump at 450° C. In addition, the curves are reversible during successive thermal cycles and the observed conductivity reductions are small compared with that for specimen (a). This is because, in the case of specimens (c) and (d), the high-temperature/low-temperature transition occurs at higher temperatures and the difference in conductivity compared with that of specimen (a) decreases at high temperature (>500° C.).

What is claimed is:

1. A process for preparing a solid composite electrolyte comprising at least one compound of the BIMEVOX family, which process comprises:

a) at least one step of preparing a mixture of one or more compounds of the BIMEVOX family with one or more chemically inert compounds, selected from the group consisting of carbides, nitrides and oxides;

b) at least one step of compacting the mixture obtained from step a); and c) at least one sintering step during which the temperature reached, over a nonzero time interval, has a value greater than the optimum sintering temperature for said compound of the BIMEVOX family;

wherein said one or more compounds of the BIMEVOX family is an oxide derived from $Bi_4V_2O_{11}$.

2. The process as claimed in claim 1, wherein the mixture from step a) comprises a nonzero amount up to 30% by volume of the one or more chemically inert compounds.

3. The process as claimed in claim 2, wherein the compound of the BIMEVOX family satisfies the formula (II):

$$(Bi_2O_2)(V_{1-y}M'_yO_z) \qquad (II)$$

in which M' represents a transition metal chosen from zinc, copper, manganese, nickel, cobalt, iron and cadmium atoms and y is greater than or equal to approximately 0.05 and less than or equal to approximately 0.5.

4. An electrochemical cell in which the solid electrolyte is obtained by the process as claimed in claim 2.

5. A process for extracting oxygen from a gas mixture containing oxygen, comprising contacting the solid composite electrolyte obtained in the process of claim 2 with the gas mixture and extracting the oxygen.

6. A process for analyzing the presence of oxygen in a gaseous atmosphere comprising contacting the solid composite electrolyte obtained in the process of claim 2 with the gaseous atmosphere.

7. The process as claimed in claim 1, wherein the compound of the BIMEVOX family satisfies the formula (II):

$$(Bi_2O_2)(V_{1-y}M'_yO_z) \tag{II}$$

in which M' represents a transition metal chosen from zinc, copper, manganese, nickel, cobalt, iron and cadmium atoms and y is greater than or equal to approximately 0.05 and less than or equal to approximately 0.5.

8. An electrochemical cell in which the solid electrolyte is obtained by the process as claimed in claim 7.

9. A process for extracting oxygen from a gas mixture containing oxygen, comprising contacting the solid composite electrolyte obtained in the process of claim 7 with the gas mixture and extracting the oxygen.

10. A process for analyzing the presence of oxygen in a gaseous atmosphere comprising contacting the solid composite electrolyte obtained in the process of claim 7 with the gaseous atmosphere.

11. An electrochemical cell in which the solid electrolyte is obtained by the process as claimed in claim 1.

12. A process for extracting oxygen from a gas mixture containing oxygen, comprising contacting the solid composite electrolyte obtained in the process of claim 1 with the gas mixture and extracting the oxygen.

13. A process for analyzing the presence of oxygen in a gaseous atmosphere comprising contacting the solid composite electrolyte obtained in the process of claim 1 with the gaseous atmosphere.

14. A process for producing ultrapure oxygen from a gas mixture containing oxygen, comprising contacting the solid composite electrolyte obtained in the process of claim 1 with the gas mixture and extracting the oxygen from the gas mixture.

15. The process as claimed in claim 1, wherein the one or more chemically inert compounds is selected from the group consisting of tungsten carbide and silicon carbide.

16. The process as claimed in claim 1, wherein the one or more chemically inert compounds is silicon nitride.

17. The process as claimed in claim 1, wherein the one or more chemically inert compounds is selected from the group consisting of titanium oxide, alumina, $BiVO_4$, zirconia, cerium oxide, hafnium oxide and thoria, said zirconia, cerium oxide, hafnium oxide or thoria being stabilized by one or more compounds selected from the group consisting of yttrium oxide, barium oxide, magnesium oxide, calcium oxide, strontium oxide, scandium oxide and lanthanum oxide.

18. The process as claimed in claim 17, wherein said zirconia is stabilized with yttrium oxide.

19. A process for removing oxygen from a gaseous atmosphere containing oxygen, said gaseous atmosphere lying above a liquid or a solid, comprising contacting the solid composite electrolyte obtained in the process of claim 1 with the gaseous atmosphere and extracting the oxygen from the gaseous atmosphere.

* * * * *